United States Patent

Kee et al.

Patent Number: 5,433,195
Date of Patent: * Jul. 18, 1995

[54] RESPIRATORY SUPPORT SYSTEM

[75] Inventors: Kok-Hiong Kee; James G. Schneider, both of St. Louis, Mo.

[73] Assignee: Sherwood Medical Company, St. Louis, Mo.

[*] Notice: The portion of the term of this patent subsequent to May 10, 2011 has been disclaimed.

[21] Appl. No.: 129,917

[22] Filed: Sep. 30, 1993

[51] Int. Cl.⁶ ............................................. A61M 25/00
[52] U.S. Cl. ................................ 128/207.14; 128/911; 128/912; 604/171; 604/35
[58] Field of Search ................... 128/202.27, 911, 912, 128/207.14, 203.12, 205.24, 207.16; 285/921, 332, 332.1; 604/35, 171

[56] References Cited

U.S. PATENT DOCUMENTS

| | | | |
|---|---|---|---|
| 3,682,166 | 8/1972 | Jacobs . | |
| 3,991,762 | 11/1976 | Radford . | |
| 4,273,126 | 6/1981 | Grane et al. | 604/319 |
| 4,275,724 | 6/1981 | Behrstock | 128/207.14 |
| 4,334,538 | 6/1982 | Juhn | 128/207.14 |
| 4,346,702 | 8/1982 | Kobuta | 128/207.14 |
| 4,462,397 | 7/1984 | Suzuki | 128/200.14 |
| 4,796,615 | 1/1989 | Bullock et al. | 128/202.27 |
| 4,805,611 | 2/1989 | Hodgkins | 128/207.14 |
| 4,865,586 | 9/1989 | Hedberg | 604/93 |
| 4,867,153 | 9/1989 | Lorenzen et al. | 128/205.12 |
| 5,025,806 | 6/1991 | Palmer et al. | 128/203.12 |
| 5,133,345 | 7/1992 | Lambert | 128/202.16 |
| 5,140,983 | 8/1992 | Jinotti | 128/207.14 |
| 5,277,177 | 1/1994 | Page et al. | 128/200.26 |
| 5,309,902 | 5/1994 | Kee et al. | 128/202.27 |

*Primary Examiner*—Edgar S. Burr
*Assistant Examiner*—William J. Deane, Jr.

*Attorney, Agent, or Firm*—Andrew J. Beck; Montgomery W. Smith; Gene B. Kartchner

[57] ABSTRACT

The invention relates to a sputum trap for an aspiration a respiratory support system which includes a sleeved suction catheter device, a suction control valve, and a ventilator manifold. The sputum trap allows collection of sputum directly from a patient through a suction catheter without causing a loss of PEEP in the respiratory support system. The sleeved suction catheter device includes a sputum trap/suction control valve end connector having a valve therein which prevents air flow through the catheter until the sputum trap or suction control valve is attached thereto. The manifold includes a one-way check valve which is opened upon insertion of the manifold end connector of the sleeved suction catheter therein. The suction control valve includes an actuator which is linearly movable between a first position in which suction therethrough is prevented, to a second position in which the valve is open to suction therethrough. The manifold includes an access port for attachment and detachment of the sleeved suction catheter thereto without interruption of continuous respiratory support of the patient. The access port has a normally closed valve therein which remains closed regardless of the pressure changes within the manifold. The normally closed valve is positioned in the port such that placement of the manifold connector of the sleeved suction catheter device therein forces the normally closed valve to an open position. The sputum trap is designed for quick connect and disconnect with the sleeved suction catheter device and the suction control valve, and for simplified sealing for subsequent transport after having been used to collect a sputum sample from a patient.

7 Claims, 2 Drawing Sheets

RESPIRATORY SUPPORT SYSTEM

BACKGROUND OF THE INVENTION

1. Field of the Invention

This invention relates generally to apparatus used in conjunction with a respiratory support system. More specifically, the present invention relates to a method and apparatus for using a suction catheter device as part of a respiratory support system such as described in copending patent applications, Ser. No. 07/962,756 filed Oct. 19, 1992 for "Respiratory Support System and Suction Catheter Device Therefor" Ser. No. 07/962,757 filed Oct. 19, 1992 for "Suction Control Valve" and Ser. No. 07/962,755 filed Oct. 19, 1992 for "Ventilator Manifold with Accessory Access Port". Even more specifically, the present invention relates to the use of a suction catheter device which includes a sputum trap attachment for collecting and transporting a sample of sputum from a patient for later analysis.

2. Prior Art

Respiratory support systems used for the ventilation of critically ill patients are now commonly used in medical facilities. Typically, a prior art respiratory support system includes a tracheal tube positioned either directly, or through the nose or mouth, into the trachea of a patient, a manifold connected to the tracheal tube at one port position thereof, and a source of breathable gas connected at a second port thereof. The purpose of the respiratory support system is to assist the patient in maintaining adequate blood oxygenation levels without overtaxing the patient's heart and lungs.

While a patient is attached to the respiratory support system, it is periodically necessary to aspirate fluid from the patient's trachea or lungs. In the past, in order to accomplish aspiration, it has been necessary to disassemble part of the respiratory support system, either by removing the ventilator manifold therefrom or by opening a port of the manifold and inserting a small diameter suction tube down the tracheal tube and into the patient's trachea and lungs. The fluid was then suctioned from the patient and the suction catheter was removed and the respiratory support system reassembled. However, due to the interruption of respiratory support during this procedure, a patient's blood oxygen often dropped to an unacceptably low level, even when other previously known breathing assistance efforts were simultaneously provided. Further, there has been no solutions offered to the problem of sputum sample collection during aspiration, which also avoids the problem of respiratory support interruption.

U.S. Pat. No. 5,073,164 to Hollister et al. is generally exemplary of the prior art of suction catheter devices. Hollister et al. includes a ventilator manifold having an access port therethrough which is adapted to receive a connector of a suction catheter device. The suction catheter device positions a catheter within the ventilator manifold without substantial manifold pressure loss. The suction catheter device includes an envelope which is positioned around the catheter portion thereof in order to prevent contamination of the catheter surface intended to be inserted into the patient's trachea and lungs.

Although this type of ventilator manifold and suction catheter device connection allows continuous respiratory support of the patient during suctioning of fluid from the patient's trachea and lungs, it nevertheless has several drawbacks associated with its use. For example, removal of the suction catheter device from the manifold, such as for the purpose of replacing the suction catheter device, or separation of the suction catheter from the suction control valve such as for the purpose of attaching a sputum trap for collecting a sputum sample from the patient cannot be accomplished without losing internal manifold pressure and compromising the integrity of the respiratory system. Since separation of the Hollister et al. suction catheter device from its suction control valve cannot be accomplished without opening the manifold to atmospheric pressure through the catheter, use of the Hollister et al. device for purposes of collecting a sputum sample from the suction catheter thereof is not possible. Instead, a separate collection device is required.

A sputum collection device of this nature which is generally exemplary of the prior art is U.S. Pat. No. 4,273,126 to Grane et al. Grane et al. includes a hand held container attached to a suction catheter at an inlet thereof and a suction source at an outlet thereof. The suction catheter is inserted into the patient's trachea and lungs and sputum is aspirated into the container. The suction catheter is then withdrawn and the sputum sample is analyzed.

As is clearly obvious, no means exist on the Grane et al. device to allow its use with a ventilator manifold in such a manner as to avoid PEEP pressure losses during sputum collection.

There therefore exists a need in the art for a respiratory support system which includes a ventilator manifold which allows simple attachment and detachment of a suction catheter device therefrom during continuous patient respiratory support, without substantial pressure loss from the manifold and without substantial collection of body fluids in the manifold. There also exists a need in the art for a sputum collection device such as a sputum trap which can be attached to, and detached from, the suction catheter device for collection of a sputum sample without causing interior pressure loss from the ventilator manifold.

OBJECTS AND SUMMARY OF THE INVENTION

A principle object of the present invention is to provide a respiratory support system which allows attachment thereto and detachment therefrom of a suction catheter device without interruption of continuous patient respiratory support.

A further object of the present invention is to provide a suction catheter device which is designed to be capable of interchangeably attaching and detaching a sputum trap for collection of a sputum sample from a patient without comprising internal manifold pressure integrity.

Another object of the present invention is to provide a suction catheter device which is capable of being disassembled from the respiratory support system to allow replacement of the suction catheter device or a component part of the respiratory support system, such as a sputum trap, during respiratory support of a patient without compromising the integrity of the ventilator manifold.

A further object of the present invention is to provide a suction catheter device which is designed to be capable of engaging a ventilator manifold at one end thereof and allowing engagement and disengagement of a suction control valve at an opposite end thereof to allow the attachment and detachment of a sputum trap thereto without compromising internal pressure integrity of the ventilator manifold.

These and other objects of the present invention are realized in a presently preferred embodiment thereof, described by way of example and not necessarily by way of limitation, which provides for interchangeable use of components of a respiratory support system and a suction catheter device during respiratory support of a patient, without comprising the integrity of the respiratory support system through loss of internal pressure in the manifold thereof. The suction catheter system preferably includes a ventilator manifold formed with an access port which includes a normally closed valve therein. The valve maintains the pressure differential between the atmosphere and the interior of the manifold regardless of manifold pressure fluctuations. The manifold also includes a pigtail type fluid injection tube which is adapted for allowing injection of fluid through the access port and the adaptor. The pigtail may also include a one-way valve therein for preventing retrograde movement of fluid therethrough.

The system also includes a suction catheter device which includes a manifold-end connector having an adaptor formed to fit within the access port of the manifold and to sealingly engage therewith. Positioning the adaptor into the access port of the manifold forces the normally closed valve therein to an open position. The access port and adaptor may include a detent and stop-type locking arrangement for locking the adaptor within the port against inadvertent withdrawal thereof during use, and for orienting the adaptor in a single unique position relative to the access port to align the side opening through the side of the access port with an opening through the side of the adaptor. The alignment of openings allows cleaning and/or lavage fluid to be injected into the interior of the adaptor and/or the interior of the manifold if desired.

The manifold-end connector allows the catheter to pass freely therethrough. The catheter itself may also include positioning marks thereon which can inform the user of the position of the distal tip of the catheter relative to the connector so that the user can readily determine how far the catheter has been inserted into the patient's trachea or lungs, or conversely, how far the catheter has been withdrawn through the connector.

The suction catheter device also includes a valve-end connector which has a septum positioned therein which closes the end of the catheter against fluid flow until the sputum trap or the suction control valve is properly attached to the thereto and forces the septum open to allow fluid flow from the catheter.

The suction catheter system further includes a sputum trap formed of a vial of preferably clear glass or plastic material having an open top into which a vial adaptor can be inserted. The vial adaptor includes connections for the sleeved suction catheter and the suction control valve and an elongate tube which extends toward the bottom of the vial when the manifold is properly inserted in the opening thereof. The tube operates as a barrier to prevent aspirated sputum which is being collected in the vial from passing into the suction control valve. The sputum trap also includes a cap which is used to seal the opening of the vial after sputum has been collected and the vial adaptor has been removed. The vial and the cap are designed to allow the cap to be stored by attachment to the bottom of the vial. If desired, the vial adaptor may also include a slit septum which is positioned in the vial adaptor in the fluid flow path between the vial and the suction control valve. The septum is positioned so that attachment of the suction control to the adaptor forces the slit valve to an open position. In this manner, when the sputum trap is used with the suction catheter system of the present invention, there can be no inadvertent loss of ventilator pressure during attachment and detachment of the sputum trap.

The suction control valve preferably includes a housing forming a fluid flow channel therethrough and an actuator for opening and closing the fluid flow passage of the housing. The actuator is normally biased to a position in which the fluid flow passage is closed to prevent fluid passage therethrough and can be actuated by the user against the biasing thereof in order to open the fluid flow passage. The actuator may also be rotated relative to the valve body to a locked position in which the actuator can no longer be actuated to cause fluid flow through the valve. A tubular extension for attachment of the valve to a suction source and to the sputum trap or the suction catheter is included on each end of the fluid flow channel through the housing.

DETAILED DESCRIPTION OF THE PREFERRED EMBODIMENT

Figure 1:
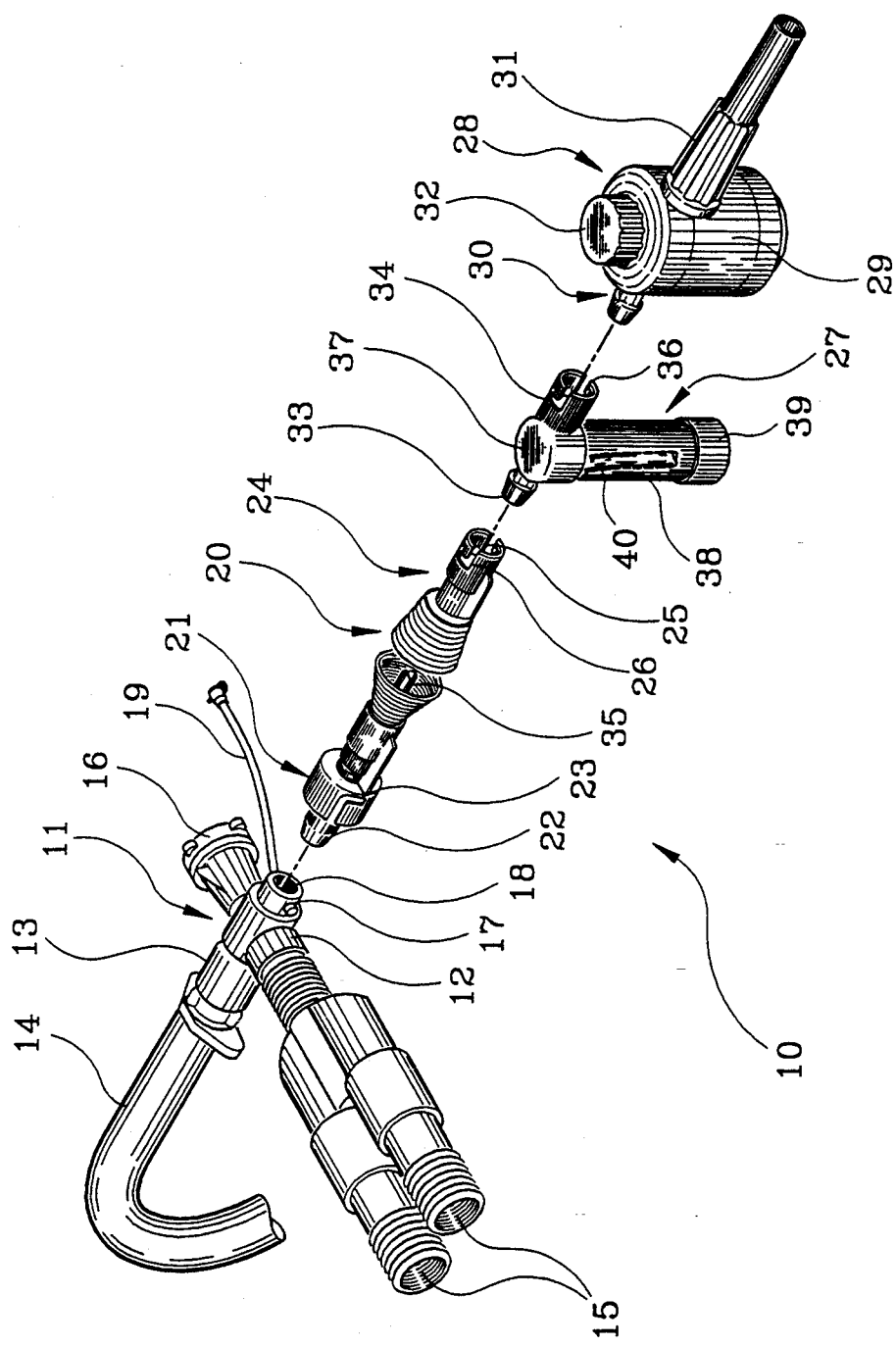
FIG. 1 is a perspective view of a suction catheter system which includes a suction control valve and a manifold of a respiratory support system attached for use to a suction catheter device, a sputum trap, and a suction control valve formed in accordance with the principles of the present invention.

As shown in the exemplary drawings for the purposes of illustration, an embodiment of a manifold, suction catheter, sputum trap, and suction control valve of a suction catheter system made in accordance with the principles of the present invention, referred to generally by the reference numeral 10, is provided for interchangeable use of the sputum trap 27 without interruption of respiratory support of the patient.

More specifically, as shown in FIG. 1, the ventilator manifold 11 includes a plurality of access ports which facilitate its connection to a ventilator circuit which is in use by the patient. The manifold 11 is attached to a patient for fluid flow communication with the patient's lungs by the connection of the patient attachment port 13 thereof to the connector of an endotracheal tube assembly 14 which has been previously positioned in the trachea of a patient by any one of several well known procedures.

Ventilator circuit connection port 12 of the manifold 11 is designed for connection to flexible breathing hoses 15 from the ventilator (not shown) in a well-known manner, such as through a "Y" site connector. Port 16 is normally capped and closed against air flow except for instances when nonpressurized ventilation is desired. The ventilator circuit provides a breathable gas mixture to the patient through one hose 15, and receives expelled air from the patient's lungs through the other hose 15. The ventilator circuit further commonly includes various valves, regulators and the like associated with the hoses 15 in order to effect respiration of the patient. The manifold 11, and hoses 15 attached thereto at the ventilator circuit connection port 12, are generally made of disposable plastic material and are generally intended to be used by only one patient and then discarded.

When attached to the patient, the entire respiratory support system 10 is designed to isolate the patient's lungs from the atmosphere and allow pressurized forced ventilation of a gas mixture of a high oxygen content from the ventilator into the patient's lungs. Commonly ventilators of this type are used to maintain a positive end expiratory pressure (PEEP) within the ventilator manifold 11 and the patient's lungs at all times during exhalation. This technique is commonly used because of its benefit of supplying a minimum concentration of oxygen to the patient at all times to maintain a proper blood oxygenation level. The PEEP procedure also keeps a large number of lung alveoli of the patient open at all times during respiratory support, thus increasing the effective lung area subject to ventilation.

The manifold 11 of the present invention includes an access port 17 which is in fluid flow communication with the interior of the manifold 11. The access port 17 includes a normally closed valve 18 preferably made of a resilient material such as rubber or silicone which maintains the interior of the manifold 11 isolated from the atmosphere at all times.

The access port 17 forms a side opening therethrough through which a pigtail fluid injection tube 19 is inserted for use in transporting fluid into the interior of the access port 17.

The sleeved suction catheter 20 includes a manifold-end connector 21, an adaptor 22, and a locking mechanism 23.

The adapter 22 and locking mechanism 23 of the connector 21 operate to attach the connector 21 to the ventilator manifold 11. Attachment of the connector 21 to the manifold 11 is effected by insertion of the adapter 22 into the access port 17 until it engages the valve 18 and forces it toward the interior of the manifold 11. Upon complete insertion of the adapter 22 into the access port 17, the valve 18 is completely open.

The valve-end connector 24 of the sleeved suction catheter device 20 includes a slit septum 25 positioned therein and normally closed. The connector 24 also includes a pair of locking slots 26 for attachment of the connector 24 to the sputum trap 27 or the suction control valve 28.

Figure 2:
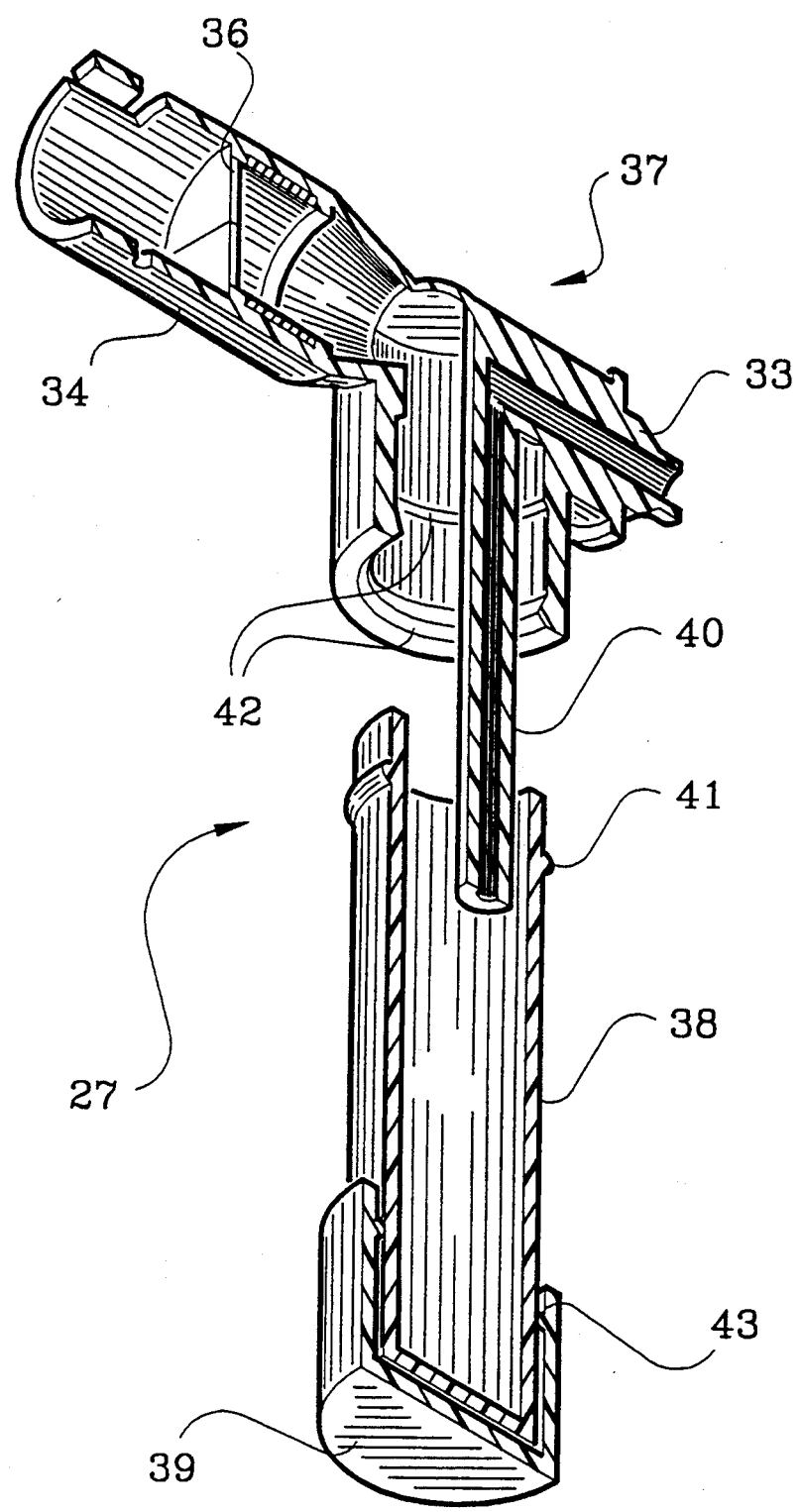
FIG. 2 is a cross sectional view of the sputum trap formed in accordance with the principles of the present invention.

As best shown in FIGS. 1 and 2, the sputum trap 27 includes a vial 38 preferably formed of a transparent plastic or glass material. The vial 38 preferably includes a rib 41 which operates as a snap fit attachment to the vial adaptor 37 in cooperation with the manifold ribs 42 in a well known manner.

The vial adaptor 37 includes a distal end connector 33 for attachment to the valve end connector 24 of the sleeved suction catheter device 20, and a proximal end connector 34 for connection with the suction catheter/sputum connector 30 of the suction control valve 28.

A normally closed slit valve 36 can be positioned within the proximal end connector 34 if desired. The slit valve 36 remains in a closed position until such time as the suction catheter/sputum trap connector 30 of the suction control valve 28 is forced therethrough during attachment of the suction control valve 28 to the vial adaptor 37 for use. When the suction control valve 28 is removed from the vial adaptor 37, the slit valve 36 returns to its normally closed position.

The vial adaptor 37 also includes a barrier tube 40 which is in fluid flow connection with the distal end connector 33 and extends a substantial distance into the vial 38 when the vial adaptor 37 is attached to the adaptor 37 for use. The barrier tube 40 forces aspirated sputum from the suction catheter 35 into the bottom of the vial 38, thus preventing it from passing directly through the sputum trap 27 into the suction control valve 28.

The sputum trap 27 also may include a cap 39 having an internal rib 43 thereon which can cooperate with the rib 41 on the vial 38 to close the vial opening after sputum has been collected in the vial 38 and the vial adaptor 37 has been removed. The vial 38 is designed to allow the cap 39 to be easily positioned around the bottom thereof for storage when not in use.

The suction control valve 28 of the present invention is formed of a valve housing 29 with a suction catheter device/sputum trap connector 30 extending away therefrom in a radial direction and a suction source connector 31 extending away therefrom in a radial direction opposite the connector 30. An actuator 32 extends from the interior of the valve housing 29. The positioning of the actuator 32 on the valve 28 is intended to allow for ease of manipulation thereof by a single hand of the user.

OPERATION OF THE PREFERRED EMBODIMENT

Operation of the respiratory support system 10 is preferably as follows. First, the ventilator manifold 11 is attached to the tracheal tube 14 which has previously been inserted into the patient's trachea, and the ventilator circuit 15 of the respiratory support system is attached to the manifold 11 in a well-known manner. The manifold-end connector 21 of the suction catheter device 20 is then inserted into the access port 17 of the manifold 11 and rotated to its locking position therewith. The suction catheter/sputum trap connector 30 of the suction control valve 28 is then inserted into the proximal end connector 34 of the sputum trap 27 and the suction control valve is then attached to a source of suction pressure through connector 31. The sputum trap distal end connector 33 is then attached to the catheter's valve end connector 24 in a similar manner. In each of the above connections, the valves 18 and 25 respectively are forced open to form a fluid flow pathway from the trachea 14 to the sputum trap 27.

When it is desired to suction the patient's trachea or lungs, the catheter 35 is advanced through the manifold-end connector 21, the manifold 11, and the tracheal tube 14 into the patient's trachea and lungs any desired distance. Aspiration of the patient's trachea and lungs is then performed by the user forcing the actuator button 32 of the suction control valve 28 downwardly into the valve housing 29 which opens the suction catheter 35 to the vacuum source through the sputum trap 27. Sputum then passes through the suction catheter 35 and into the sputum trap 27 by way of the barrier tube 40 of the vial adaptor 37.

When it is desired to remove the sputum trap 27 from the suction catheter system, the proximal and distal end connectors 34 and 33 thereof are detached from the suction control valve 28 and suction catheter device 20 respectively. The vial adaptor 37 can then be removed from the vial 38, and the cap 39 can be removed from the bottom of the vial 38 and snap fitted over the vial opening. The vial is then ready for transport of the sputum for subsequent analysis.

Once the sputum trap 27 is removed, the suction catheter/sputum connector 30 of the suction control valve 28 can be attached to the valve end connector 24 of the suction catheter device 20 and the system 10 can continue to be used for suctioning the patient as desired. In this configuration, pushing the actuator 32 of the suction control valve 28 downwardly causes suction to be drawn directly through the suction catheter 35 and the control valve 28.

When the actuator 32 is released after suctioning through the suction catheter device 20 is completed, the actuator 32 moves upwardly to again close of the suction source from the catheter 35.

Once the catheter 35 is withdrawn from the patient, the medical worker may clean the distal end of the catheter 35 by injecting fluid through the pigtail 19 and activating the suction control valve 28. Alternatively, a medical worker may inject lavage fluid through the pigtail 19 and allow it to pass into the manifold 11 and down the patient's trachea and lungs, and thereafter insert the catheter 35 into the patient's trachea and lungs and aspirate the patient to remove the lavage fluid.

When it becomes necessary to remove the suction catheter device 20 from the manifold 11, the manifold-end connector 21 is merely detached from the access port 17 and withdrawn therefrom. Alternatively, if it becomes necessary to replace the suction control valve 28, it can be disconnected from the valve-end connector 24 and replaced. It is important to note that in any instance of removal of a component of the system 10, i.e., the sleeved suction catheter device 20, the sputum trap 27, or the suction control valve 28, no loss of PEEP from the manifold 11 occurs due to the normally closed manifold valve 18 of the manifold 11, the slitted septum 25 of the valve-end connector 24 and/or the normally closed slit septum 36 of the sputum trap 27.

It should be understood from the foregoing that, while a particular embodiment of the invention has been illustrated and described, various modifications can be made thereto without departing from the spirit and scope of the invention. Therefore, it is not intended that the invention be limited by the specification; instead, the scope of the present invention is intended to be limited only by the appended claims.

We claim:

1. An aspiration device comprising:
    a manifold adapted to be connected for fluid flow attachment between a patient and a ventilator circuit,
    a sleeved suction catheter including a manifold end connector and a sputum trap suction control valve end connector,
    a sputum trap including a distal end connector and a proximal end connector, and,
    a suction control valve,
    said manifold end connector being adapted for connection with said manifold, said sputum/suction control valve end connector including a normally closed valve located therein for preventing fluid flow through said sleeved suction catheter when said normally closed valve is in its normally closed position and for allowing fluid flow through said sleeved suction catheter when said normally closed valve is forced to an opened position due to attachment of said sputum trap/suction control valve end connector to said suction control valve, said sputum trap/suction control valve end connector being adapted for connection alternating between said sputum trap and said suction control valve.

2. An aspiration device according to claim 1 wherein said manifold includes an access port for allowing attachment of said manifold end connector of said sleeved suction catheter to said manifold, said access port being normally closed against fluid flow therethrough,
    whereby, attachment of said manifold end connector to said access port operates to open said access port to allow fluid flow access between said manifold and said sleeved suction catheter.

3. An aspiration device according to claim 2 wherein said access port includes a normally closed valve therein,
    whereby, said normally closed valve is closed to fluid flow through said access port and is forced to an open position by said manifold end connector of said sleeved suction catheter to allow fluid flow through said access port when said manifold end connector is properly positioned within said access port.

4. An aspiration device according to claim 2 wherein said manifold end connector includes an adaptor for opening said normally closed valve of said access port.

5. A sputum trap for use with a suction catheter device for collection of sputum from a patient's trachea or lungs, said sputum trap comprising:
    a collection vial for collecting sputum, said vial having a top and a bottom, said top of said vial including an opening, and
    an adaptor for attachment to said top of said vial over said opening, said adapter including a proximal end connector for attachment to a suction catheter, and a distal end connector for attachment to a suction control device, said proximal end connector of said adapter further including a normally closed valve therein which is movable to an open position upon connection of the suction control device to said proximal end connector,
    whereby, when said adapter is attached to said top of said vial over said opening and the suction catheter and suction control device are attached to said distal and proximal ends respectively of said adapter, suction can be drawn through said sputum trap to aspirate sputum from a patient's trachea or lungs through the suction catheter into said vial.

6. A sputum trap according to claim 5 wherein said adaptor includes a fluid flow barrier which operates to allow sputum to flow into said vial from the suction catheter but inhibits sputum from flowing out of said vial to the suction control device.

7. A sputum trap according to claim 6 wherein said fluid flow barrier in said adaptor includes an elongate tube which extends a substantial distance into said vial.

* * * * *